(12) United States Patent
Pimenta et al.

(10) Patent No.: US 11,147,751 B2
(45) Date of Patent: *Oct. 19, 2021

(54) FLUID COMPOSITIONS COMPRISING A STRUCTURING AGENT

(75) Inventors: Paloma Pimenta, Staten Island, NY (US); Jason Nesta, Cedar Knolls, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/997,344

(22) PCT Filed: Dec. 23, 2010

(86) PCT No.: PCT/US2010/061960
§ 371 (c)(1),
(2), (4) Date: Jun. 24, 2013

(87) PCT Pub. No.: WO2012/087326
PCT Pub. Date: Jun. 28, 2012

(65) Prior Publication Data
US 2013/0272970 A1    Oct. 17, 2013

(51) Int. Cl.
| | | |
|---|---|---|
| *A61K 8/04* | (2006.01) | |
| *A61K 8/73* | (2006.01) | |
| *A61Q 11/00* | (2006.01) | |
| *C08B 37/00* | (2006.01) | |
| *A61K 8/81* | (2006.01) | |
| *A61K 8/25* | (2006.01) | |
| *A61K 9/00* | (2006.01) | |

(52) U.S. Cl.
CPC .............. *A61K 8/044* (2013.01); *A61K 8/042* (2013.01); *A61K 8/25* (2013.01); *A61K 8/73* (2013.01); *A61K 8/731* (2013.01); *A61K 8/8152* (2013.01); *A61Q 11/00* (2013.01); *C08B 37/006* (2013.01); *C08B 37/0033* (2013.01); *A61K 9/0014* (2013.01)

(58) Field of Classification Search
None
See application file for complete search history.

(56) References Cited

U.S. PATENT DOCUMENTS

| | | | |
|---|---|---|---|
| 3,943,063 A | 3/1976 | Morishita et al. | |
| 5,137,729 A | 8/1992 | Kuroya et al. | |
| 5,562,939 A | 10/1996 | Lewis | |
| 5,776,435 A | 7/1998 | Gaffar et al. | |
| 6,106,883 A | 8/2000 | Sokolik et al. | |
| 6,153,210 A | 11/2000 | Roberts et al. | |
| 6,595,997 B2 | 7/2003 | Axelson, Jr. et al. | |
| 6,596,298 B2 | 7/2003 | Leung et al. | |
| 6,602,841 B1 | 8/2003 | Becker et al. | |
| 6,669,929 B1 | 12/2003 | Boyd et al. | |
| 6,682,721 B2 | 1/2004 | Kim et al. | |
| 6,683,067 B2 | 1/2004 | Lawter et al. | |
| 7,008,979 B2 | 3/2006 | Schottman et al. | |
| 7,241,411 B2 | 7/2007 | Berry et al. | |
| 7,357,891 B2 | 4/2008 | Yang et al. | |
| 7,723,430 B2 | 5/2010 | Kunitake et al. | |
| 2001/0006624 A1 | 7/2001 | Witt et al. | |
| 2002/0041852 A1 | 4/2002 | Napolitano et al. | |
| 2003/0091514 A1* | 5/2003 | Stier | 424/48 |
| 2003/0124065 A1 | 7/2003 | Majeti et al. | |
| 2003/0215401 A1 | 11/2003 | Estrada et al. | |
| 2005/0210615 A1* | 9/2005 | Shastry et al. | 15/210.1 |
| 2006/0110416 A1 | 5/2006 | Ryles et al. | |
| 2006/0122082 A1 | 6/2006 | Leonard | |
| 2007/0044824 A1 | 3/2007 | Capeci et al. | |
| 2007/0053849 A1 | 3/2007 | Doyle et al. | |
| 2009/0068259 A1 | 3/2009 | Pilch et al. | |
| 2009/0238777 A1 | 9/2009 | Joziak et al. | |
| 2009/0269288 A1 | 10/2009 | Lavrova | |
| 2010/0076080 A1 | 3/2010 | Yelm et al. | |

FOREIGN PATENT DOCUMENTS

| | | |
|---|---|---|
| CN | 1913862 | 2/2007 |
| DE | 202008006245 | 8/2008 |
| JP | H08-337518 A | 12/1996 |
| JP | 2009-102282 | 5/2009 |
| JP | 2009-102283 | 5/2009 |
| WO | WO 95/020971 | 8/1995 |
| WO | WO 00/010527 | 3/2000 |
| WO | WO 05/041876 | 5/2005 |
| WO | WO 2006/013081 | 2/2006 |
| WO | WO 12/087324 | 6/2012 |
| WO | WO 12/087325 | 6/2012 |

(Continued)

OTHER PUBLICATIONS

Medina-Torres et al., "Rheology of sodium polyacrylate as an emulsifier employed in cosmetic emulsions", I & EC Research, 2014, p. 18346-18351.*

(Continued)

*Primary Examiner* — Kyung S Chang

(57) ABSTRACT

The present invention provides mouthwash or mouthrinse compositions comprising one or more structuring agents selected from: a colloidal gum, a cellulosic polymer, an acrylate polymer, or a clay or fine particulate, and an orally acceptable aqueous carrier. In some embodiments, the total concentration of the one or more structuring agents is less than 5%, by weight, of the composition.

12 Claims, No Drawings

(56) References Cited

FOREIGN PATENT DOCUMENTS

| WO | WO 12/087327 | 6/2012 |
| WO | WO 12/087328 | 6/2012 |

OTHER PUBLICATIONS

International Search Report and Written Opinion in International Application No. PCT/US2010/061960, dated Nov. 25, 2011.
Pangborn et al., 1978, "Effect of Hydrocolloids on Apparent Viscosity and Sensory Properties of Selected Beverages," J. Texture Studies 9(4):415-436.
Soci et al., 1980, "Influence of Viscosity on Absorption from Nitrofurantoin Suspensions," J. Pharmaceutical Science 69(4):403-406.
Written Opinion in International Application No. PCT/US2010/061960, dated Nov. 30, 2012.

\* cited by examiner

FLUID COMPOSITIONS COMPRISING A STRUCTURING AGENT

BACKGROUND

Aqueous compositions are used for delivery of a variety of compounds to the oral cavity. The ability to incorporate certain compounds in aqueous compositions may be limited because such compounds may be insoluble or have limited solubility in a water based composition.

Currently available aqueous compositions have rheological properties similar to water. The benefits of an aqueous composition can be improved by modulating its rheological properties. The compositions described are directed to, inter alia, that end.

SUMMARY

In some embodiments, the present invention provides oral fluid compositions that have physical properties which make them particularly useful in providing various aspects desirable for such products. In some embodiments, structuring agents, such as polymers or clays, are used to achieve specific rheological characteristics that provide certain advantages over non-structured aqueous compositions.

In some embodiments, the fluid compositions are structured and viscoelastic. As such, the fluid compositions can maintain solids in suspension. In other embodiments, the viscoelastic properties provide good mouth feel during and after use.

Some embodiments provide a fluid composition comprising: one or more structuring agents selected from: a gum-type colloidal polymer; a cellulosic polymer; an acrylate polymer; and a clay or fine particulate; and an orally acceptable aqueous carrier; wherein the composition has a G' to G" ratio of greater than or equal to 1. In some embodiments, the total concentration of the one or more structuring agents is less than 5%, by weight, of the composition.

Some embodiments provide methods of treating or preventing a disease or condition of the oral cavity comprising contacting an oral cavity surface with any of the compositions described herein.

DETAILED DESCRIPTION

As used throughout, ranges are used as shorthand for describing each and every value that is within the range. Any value within the range can be selected as the terminus of the range.

All references cited herein are hereby incorporated by reference in their entireties. In the event of a conflict in a definition in the present disclosure and that of a cited reference, the present disclosure controls.

As used herein, the term "viscoelastic fluid" refers to a complex fluid that exhibits mechanical properties that are both elastic (solid-like e.g. rubber) and viscous (liquid-like, flowable e.g. water). A viscoelastic fluid composition will deform and flow under the influence of an applied shear stress (e.g. shaking or swishing in the mouth), but when the stress is removed the composition will recover from the deformation. The elastic portion of the viscoelastic behavior is quantified by the elastic modulus (G'), while the viscous portion is quantified by the viscous modulus (G").

As used herein, the term "shear thinning" refers to a property in which viscosity decreases with increasing rate of shear stress. Materials that exhibit shear thinning properties are called pseudoplastic.

As used herein, "structured fluid" and "structured composition" may be used interchangeably, and refer to a fluid that exhibits a G' value greater than the G" value (i.e. the ratio of G' to G" is >1) within the linear viscoelastic region of a strain sweep measurement. The ratio of G' to G" has been identified as the Structural Parameter.

In some embodiments, fluid compositions are provided that contain one or more structuring agents that form a viscoelastic network with specific rheological characteristics.

As used herein, the term "structuring agent" refers to a substance which is able to form by itself, or in combination with another substance, a structured network in an aqueous medium, and provide a $G'/G" \geq 1$.

In some embodiments, the fluid compositions of the present invention demonstrate non-Newtonian rheology, i.e. they behave like a power law fluid. In some embodiments, they are also characterized by a low Consistency Index and a Structural Parameter equal to or greater than 1. There are certain clear advantages of formulating a non-Newtonian, structured aqueous composition over a common Newtonian, non-structured product. For example, structured aqueous compositions provide the ability to suspend solid materials (e.g., inorganic actives, or aesthetic components like beads, strips, pigments etc.) via an alternative path that does not involve density matching, which is often limiting. Some embodiments provide structured aqueous compositions. In some embodiments, the structured aqueous compositions enable the modification of consumer perceived mouth feel attributes upon usage.

Some embodiments provide a fluid composition comprising: one or more structuring agents selected from: a gum-type colloidal polymer; a cellulosic polymer; an acrylate polymer; and a clay or fine particulate; and an orally acceptable aqueous carrier; and wherein the composition has a G' to G" ratio of greater than or equal to 1.

In some embodiments, the total concentration of the one or more structuring agents is less than about 5%, by weight, of the composition. In some embodiments, the total concentration of the one or more structuring agents is less than about 4.5%, by weight, of the composition. In some embodiments, the total concentration of the one or more structuring agents is less than about 4%, by weight, of the composition. In some embodiments, the total concentration of the one or more structuring agents is less than about 3.5%, by weight, of the composition. In some embodiments, the total concentration of the one or more structuring agents is less than about 3%, by weight, of the composition. In some embodiments, the total concentration of the one or more structuring agents is less than about 2.5%, by weight, of the composition. In some embodiments, the total concentration of the one or more structuring agents is less than about 2%, by weight, of the composition. In some embodiments, the total concentration of the one or more structuring agents is less than about 1.5%, by weight, of the composition. In some embodiments, the total concentration of the one or more structuring agents is less than about 1%, by weight, of the composition. In some embodiments, the total concentration of the one or more structuring agents is less than about 0.5%, by weight, of the composition. In some embodiments, the total concentration of the one or more structuring agents is less than about 0.3%, by weight, of the composition. In some embodiments, the total concentration of the one or more structuring agents is less than about 0.25%, by weight, of the composition. In some embodiments, the total concentration of the one or more structuring agents is less than about 0.2%, by weight, of the composition. In some embodiments, the total concentration of the one or more structuring agents is less than about 0.15%, by weight, of the composition.

In some embodiments, the total concentration of the one or more structuring agents is from about 0.03 to about 2%, by weight, of the composition. In some embodiments, the total concentration of the one or more structuring agents is from about 0.08 to about 04%, by weight, of the composition. In some embodiments, the total concentration of the one or more structuring agents is from about 0.22 to about 0.3%, by weight, of the composition. In some embodiments, the total concentration of the one or more structuring agents is about 0.12%, by weight, of the composition. In some embodiments, the total concentration of the one or more structuring agents is about 0.26%, by weight, of the composition. In some embodiments, the total concentration of the one or more structuring agents is about 0.5%, by weight, of the composition.

As used herein, the term "fluid composition" refers to a composition having the ability to take on the shape of its container.

As used herein, the term "aqueous" refers to a free water content of at least about 40%, by weight.

In some embodiments, at least one of the one or more structuring agents is a gum-type colloidal polymer. In some embodiments, the gum-type colloidal polymer is selected from: agar, agarose, albumin, algae colloid, alginates, alginic acid and salts thereof, amber, ammoniac, amylopectins, arabinans, arabinogalactan, arabinoxylans, asafetida, bdellium, carageenans, casein, chicle, collagen, copal, curdlan, dermatin sulfate, dextrans, cross-linked dextrans, dextrin, emulsan, gelatin, fenugreek, frankincense, furcellarans, galactoglucomannans, galactomannans, gamboge, gellan, gellan gum, glucomannans, glycogens, guar, guar gum, hydroxypropylated guar gums, carboxymethyl guar gum, carboxymethyl(hydroxypropyl) guar gum, hydroxyethyl guar gum, gum arabic, gum elastic, gum ghatti, gum karaya, gum tragancanth (tragacanthin), heparin, hyaluronic acid, India rubber, inulin, karaya gum, keratin sulfate, konjac flour, konjac mannan, labdanum, laminarans, laurdimonium, laxseed saccharide (acidic), levan, locust bean gum, myrrh, okra gum, pectic acids, pectin, polydextrose, polyquaternium-4, polyquaternium-10, polyquaternium-28, protopectins, psyllium seed gum, pullulan, quince seed gum, sodium hyaluronate, raffinose, rhamsan, scleroglucan, sodium alginate, stachylose, starch from rice, corn, potato or wheat, tapioca starch, succinoglycan, tamarind seed gum, trant gum, water-soluble soybean polysaccharide, whelan, xanthan, xanthan gum, xylans, xyloglucans, and mixtures thereof.

Further embodiments provide compositions wherein at least one of said one or more structuring agents is a cellulosic polymer. In some embodiments, the cellulosic polymer is selected from: cellulose; methyl cellulose; ethyl cellulose; propyl cellulose; butyl cellulose; carboxymethyl cellulose; carboxyethyl cellulose; carboxymethyl methyl cellulose; carboxyethyl ethyl cellulose; carboxyethyl methyl cellulose; carboxymethyl ethyl cellulose; hydroxyalkyl cellulose; hydroxymethyl cellulose; hydroxyethyl cellulose; hydroxypropyl cellulose; hydroxybutyl cellulose; hydroxymethyl methyl cellulose; hydroxyethyl methyl cellulose; hydroxypropyl methyl cellulose; hydroxybutyl methyl cellulose; hydroxymethyl ethyl cellulose; hydroxyethyl ethyl cellulose; hydroxypropyl ethyl cellulose; hydroxybutyl ethyl cellulose; hydroxymethyl propyl cellulose; hydroxyethyl propyl cellulose; hydroxypropyl propyl cellulose; hydroxybutyl propyl cellulose; hydroxymethyl butyl cellulose; hydroxyethyl butyl cellulose; hydroxypropyl butyl cellulose; hydroxybutyl butyl cellulose; hydroxypropyl oxyethyl cellulose; steardimonium hydroxyethyl cellulose; cocodimonium hydroxypropyl oxyethyl cellulose; sodium carboxymethyl cellulose; nitrocellulose; sodium cellulose sulfate; chondroitin; chitin; chitosan; chitosan pyrrolidone carboxylate; chitosan glycolate chitosan lactate and mixtures thereof.

Yet other embodiments provide compositions wherein at least one of said one or more structuring agents is an acrylate polymer. In some embodiments, the acrylate polymer is selected from: homopolymers of acrylic acid, crosslinked with an allyl ether pentaerythritol, allyl ether of sucrose or allyl ether of propylene, polyvinyl methylether, and carboxyvinyl polymer; polyoxyethylene polymers; polyoxyethylene/polyoxypropylene copolymers; acrylic polymers such as sodium polyacrylate, polyethyl acrylate, and polyacrylamide; synthetic water-soluble polymers such as polyethyleneimine and other kind of cationic polymers; semi-synthetic water-soluble polymers such as silicone-modified pulllan; and water-soluble inorganic polymers such as, bentonite, aluminum magnesium silicate, montmorillonite, beidellite, notronite, saponite, hectorite, and silicic anhydride. The examples of other water-soluble polymer include polyvinyl alcohol and polyvinyl pyrrolidone and mixtures thereof.

While other embodiments provide compositions wherein at least one of said one or more structuring agents is a clay or fine particulate. In some embodiments, the clay or fine particulate is selected from: calcium magnesium silicate and amorphous silica.

In some embodiments, the composition further comprises a humectant. In some embodiments, the humectant is selected from: sorbitol, glycerin, propylene glycol, ethanol, and a combination of two or more thereof.

In some embodiments, the orally acceptable aqueous carrier comprises from about 40 to about 97%, by weight, free water. In some embodiments, the orally acceptable carrier comprises greater than about 40%, by weight, free water. In some embodiments, the orally acceptable carrier comprises greater than about 45%, by weight, free water. In some embodiments, the orally acceptable carrier comprises greater than 50%, by weight, free water. In some embodiments, the orally acceptable carrier comprises greater than about 55%, by weight, free water. In further embodiments, the orally acceptable aqueous carrier comprises greater than 60%, by weight, free water. In some embodiments, the orally acceptable carrier comprises greater than about 65%, by weight, free water. In some embodiments, the orally acceptable carrier comprises greater than about 70%, by weight, free water. In some embodiments, the orally acceptable carrier comprises about 70%, by weight, free water. In some embodiments, the orally acceptable carrier comprises about 71%, by weight, free water. In some embodiments, the orally acceptable carrier comprises about 72%, by weight, free water. In some embodiments, the orally acceptable carrier comprises about 73%, by weight, free water. In some embodiments, the orally acceptable carrier comprises about 74%, by weight, free water. In some embodiments, the orally acceptable carrier comprises about 75%, by weight, free water. In some embodiments, the orally acceptable carrier comprises greater than about 75%, by weight, free water. In some embodiments, the orally acceptable carrier comprises greater than about 80%, by weight, free water. In some embodiments, the orally acceptable carrier comprises greater than about 85%, by weight, free water. In some embodiments, the orally acceptable carrier comprises greater than about 90%, by weight, free water. In some embodiments, the orally acceptable carrier comprises greater than about 90%, by weight, free water.

In some embodiments, the water to humectant ratio is from about 20:1 to about 1:5. In some embodiments, the water to humectant ratio is from about 10:1 to about 1:3. In some embodiments, the water to humectant ratio is from about 4:1 to about 2:3.

In some embodiments, the composition further comprises one or more components selected from a fluoride ion source; a tartar control agent; an antibacterial agent; a buffering agent; an abrasive; and a combination of two or more thereof. Some embodiments provide compositions wherein at least one of the one or more components is a fluoride ion source selected from: stannous fluoride, sodium fluoride, potassium fluoride, sodium monofluorophosphate, sodium fluorosilicate, ammonium fluorosilicate, amine fluoride, ammonium fluoride, and a combination of two or more thereof.

Some embodiments provide a composition comprising: from about 0.01 to about 0.5%, by weight, of a gum-type colloidal polymer; from about 0.01 to about 0.5%, by weight, of a cellulosic polymer; and from about 0.01 to about 0.5%, by weight, of an acrylate polymer.

Other embodiments provide a composition comprising: from about 0.03 to about 0.1%, by weight, of a gum-type colloidal polymer; from about 0.02 to about 0.1%, by weight, of a cellulosic polymer; and from about 0.03 to about 0.1%, by weight, of an acrylate polymer.

Further embodiments provide a composition comprising: about 0.04%, by weight, of a gum-type colloidal polymer; about 0.03%, by weight, of a cellulosic polymer; and about 0.05%, by weight, of an acrylate polymer.

Still other embodiments provide a composition comprising: 0.041%, by weight, of a gum-type colloidal polymer; 0.03%, by weight, of a cellulosic polymer; and 0.05%, by weight, of an acrylate polymer.

In some embodiments, the gum-type colloidal polymer is xanthan gum; the cellulosic polymer is carboxymethyl cellulose; and the acrylate polymer is carbomer.

Some embodiments provide a composition comprising: from about 0.01 to about 0.5%, by weight, of a first gum-type colloidal polymer; from about 0.01 to about 0.5%, by weight, of a second gum-type colloidal polymer; from about 0.01 to about 0.5%, by weight, of a cellulosic polymer; and from about 0.01 to about 0.5%, by weight, of an acrylate polymer.

Other embodiments provide a composition comprising: from about 0.05 to about 0.1%, by weight, of said first gum-type colloidal polymer; from about 0.03 to about 0.1%, by weight, of said second gum-type colloidal polymer; from about 0.05 to about 0.1%, by weight, of a cellulosic polymer; and from about 0.03 to about 0.1%, by weight, of an acrylate polymer.

In some embodiments, the composition comprises: from about 0.07 to about 0.09%, by weight, of a first gum-type colloidal polymer; from about 0.04 to about 0.06%, by weight, of a second gum-type colloidal polymer; from about 0.07 to about 0.09%, by weight, of a cellulosic polymer; and from about 0.04 to about 0.06%, by weight, of an acrylate polymer.

Some embodiments provide a composition comprising: about 0.08%, by weight, of a first gum-type colloidal polymer; about 0.05%, by weight, of a second gum-type colloidal polymer; about 0.08%, by weight, of a cellulosic polymer; and about 0.05%, by weight, of an acrylate polymer.

Yet other embodiments provide a composition comprising: 0.083%, by weight, of a first gum-type colloidal polymer; 0.05%, by weight, of a second gum-type colloidal polymer; 0.083%, by weight, of a cellulosic polymer; and 0.05%, by weight, of an acrylate polymer.

In some embodiments, the first gum-type colloidal polymer is xanthan gum; the second gum-type colloidal polymer is gellan gum; the cellulosic polymer is carboxymethyl cellulose; and the acrylate polymer is carbomer.

In some embodiments, the clay or fine particulate is present in the composition at a concentration of from about 0.1 to 2%, by weight. In some embodiments, the clay or fine particulate is present in the composition at a concentration of 0.5%, by weight.

In some embodiments, the composition comprises a suspended material. In some embodiments, the suspended material is selected from: a colloidal metal; a film flake; a film strip; and a combination of two or more thereof.

In some embodiments, the composition is a mouthwash or mouthrinse.

Some embodiments provide a method of treating or preventing a disease or condition of the oral cavity comprising contacting an oral cavity surface of a subject in need thereof, with any one of the compositions described herein. In some embodiments, the disease or condition of the oral cavity is xerostomia.

Two tests are utilized to obtain the rheology profile of viscoelastic fluid compositions, a strain sweep and a flow test. The strain sweep test indicates whether an aqueous composition is structured or not. The flow test measures shear thinning and consistency. Balancing the degree of shear thinning and consistency can be used to set out parameters to achieve preferred mouth feel characteristics.

A strain sweep test measures $G'$ and $G''$ respectively. Taking the ratio of the $G'$ value to the $G''$ value within a linear viscoelastic region gives the so called "Structural Parameter." In some embodiments, the present invention provides a composition having a $G'$ to $G''$ ratio of greater than about 1.5. In some embodiments, the $G'$ to $G''$ ratio is greater than about 2.5.

The second test is the flow test, and this test is utilized to quantify the viscoelastic shear thinning behavior of a composition. The flow test measures the fluid viscosity as a function of shear rate and measurements disclosed herein were conducted within a shear rate range of $0.1$-$100$ $sec^{-1}$. The shear thinning behavior can be quantified by fitting the flow curve to a power law function and looking at the Flow Rate Index ("n"). The flow rate index for a Newtonian fluid like water is 1, while for shear thinning fluids n is less than 1.

In some embodiments, the composition has a Flow Rate Index of less than 1. In other embodiments, the composition has a Flow Rate Index of from about 0.1 to about 0.8. In some embodiments, the composition has a Flow Rate Index of from about 0.2 to about 0.7. In further embodiments, the composition has a Flow Rate Index of about 0.7.

In some embodiments, the composition has a Flow Rate Index of from about 0.3 to about 0.6. In some embodiments, the composition has a Flow Rate Index of about 0.4. Still further embodiments provide compositions having a Flow Rate Index of about 0.5.

The Consistency Index ("k") is also quantified based on the power law fit, and should range between 10 cps<k<2000 cps. The combination of a Flow Rate Index of less than 1, and Consistency Index of greater than 10, is responsible, in part, for the desirable characteristics provided by compositions described herein.

In some embodiments, the Consistency Index is about two orders of magnitude greater than the Consistency Index of water. The combination of a Flow Rate Index of less than 1, and Consistency Index of greater than 10, is responsible, in part, for the desirable characteristics provided by compositions described herein.

In some embodiments, the compositions of the present invention have: 1) a G' to G" ratio greater than or equal to 1, greater than about 1.5, greater than about 2.5, or greater than about 3.5; 2) a Flow Rate Index from about 0.1 to about 0.85, or from about 0.3 to about 0.7; and 3) a Consistency Index from about 10 to about 2000.

The components suitable for preparing the compositions described herein with the required rheological properties may be designed as follows. One or more structuring agents can be combined in amounts and ratios which maintain the composition as a fluid when mixed with water or a combination of water and a humectant.

The terms "gum-type colloidal polymer(s)" and "colloidal gums" are used interchangeably and generally refer to any of the wide variety of colloidal substances which share general characteristics. Gums are typically extracted from or exuded by plants. True gums are complex organic substances most typically derived from plants. Some gums are water soluble in water while insoluble gums often can swell and adsorb water. Their chemical nature is complex. They are generally complex polysaccharides which often contain salts of various metals such as calcium, magnesium, and potassium in the form of salts of various organic acids. In addition to true gums, other colloidal substances such as gum resins and mixtures of gums and gum resins may be used as well as other gum-like substances derived from other organisms or synthesized.

Acrylate polymers and copolymers include, but are not limited to, synthetic high molecular weight polymers of acrylic acid known as carbomer including homopolymers of acrylic acid, crosslinked with an alkyl ether pentaerythritol, allyl ether of sucrose or allyl ether of propylene. Carbomer has a USP classification of "carbomer homopolymer Type A". Carbomers have the ability to absorb, retain water and swell to many times their original volume. Carbomers codes (910, 934, 940, 941, 971, 974 and 934P) are an indication of molecular weight and the specific components of the polymer.

When mixed with water, or water plus humectants, in proper amounts and proportions, the one or more structuring agents described herein, the composition remains as a fluid. Rather the fluid composition is a structured, and able to maintain solid particles in suspension by virtue of, among other things, a network of the structuring agents. In some embodiments, the fluid compositions described herein are also viscoelastic. When force is added such as the swishing and gargling action typical of mouthwash use, the compositions experience shear thinning and become much less viscous. This provides greater spreadability within and throughout the oral cavity, placing the composition in contact with tissue and teeth. When the force is discontinued, the composition rapidly returns to its more viscous state which coats surfaces within the oral cavity, thereby providing good mouth feel and relief of dry mouth symptoms.

In some embodiments, water makes up the largest portion of the fluid composition. However, other components, e.g. humectants, can be substituted for water; and in combination with the structuring agents described herein, can provide the desired rheological profile of the compositions of the present invention.

Other humectants such as polyol and sugar alcohol solutions may be present in amount of from about 1 to about 25% each, by weight. Sorbitol and/or another sugar alcohol are generally present, typically from about 1 to about 25%, by weight. In some embodiments, sorbitol is present at a concentration of from about 5 to about 15%, by weight. In other embodiments, sorbitol is present at a concentration of about 10%, by weight. Reference to sorbitol herein refers to the material typically available commercially as a 70% aqueous solution.

In some embodiments, glycerin and/or a similar polyol are present at a concentration of from about 1 to about 25% each, by weight. In some embodiments, glycerin is present at a concentration of from about 5 to about 15%, by weight. Some embodiments provide compositions wherein glycerin is present at a concentration of about 7.5%, by weight.

In some embodiments, the total humectant concentration is from about 1 to about 60%, by weight of the composition.

Another solvent, the diol propylene glycol, may be present. When present, propylene glycol is typically present at a concentration of from about 0.1 to about 50%, by weight. In some embodiments propylene glycol is present at a concentration of from about 5 to about 15%, by weight. Some embodiments have propylene glycol present at a concentration of about 7%, by weight. Other examples of humectant polyols include, but are not limited to: ethylene glycol; polyols, e.g. dipropylene glycol and hexylene glycol; cellosolves such as methyl cellosolve and ethyl cellosolve; vegetable oils and waxes containing at least about 12 carbons in a straight chain such as olive oil, castor oil and petrolatum; and esters such as amyl acetate, ethyl acetate and benzyl benzoate.

Whether included as an additive or derived from one or more of the various polymer and clay components that may be present, the fluid composition typically contains a cation such as for example sodium, potassium, calcium and magnesium. The concentration of cation such as sodium present is generally about 1%, by weight, or less. In some embodiments, the concentration of a cation such as sodium is about 0.5%, by weight, or less.

Other optional additives may be included. Among such optional additives, included are those provided in order to change appearance or aesthetic appeal, and/or to preserve the final product, and/or for taste/cosmetic appeal and/or as therapeutic and prophylactic ingredients for oral health, prevention or treatment of a condition or disorder of hard or soft tissue of the oral cavity, or the prevention or treatment of a physiological disorder or condition.

Some embodiments provide a composition wherein a preservative is present. In some embodiments, the preservative is selected from parabens, potassium sorbate, benzyl alcohol, phenoxyethanol, polyaminopropryl biguanide, caprylic acid, sodium benzoate and cetylpyridinium chloride. In some embodiments, the preservative is present at a concentration of about 0.0001 to about 1%, by weight. In some embodiments, the preservative is present at about 0.5%, by weight. In some embodiments, the preservative is cetylpyridinium chloride.

Colorants such as dyes may be food color additives presently certified under the Food Drug & Cosmetic Act for use in food and ingested drugs, including dyes such as FD&C Red No. 3 (sodium salt of tetraiodofluorescein), Food Red 17, disodium salt of 6-hydroxy-5-{(2-methoxy-5-methyl-4-sulphophenyl)azo}-2-n-aphthalenesulfonic acid, Food Yellow 13, sodium salt of a mixture of the mono and disulphonic acids of quinophtalone or 2-(2-quinolyl) indanedione, FD&C Yellow No. 5 (sodium salt of 4-p-sulfophenylazo-1-p-sulfophenyl-5-hydroxypyrazole-3 carboxylic acid), FD&C Yellow No. 6 (sodium salt of p-sulfophenylazo-B-naphtol-6-monosulfonate), FD&C Green No. 3

(disodium salt of 4-{[4-(N-ethyl-p-sulfobenzylamino)-phenyl]-(4-hydroxy-2-1-sulfoniumphenyl)-methylene}-[1-(N-ethyl-N-p-sulfobenzyl)-.DELTA.-3,5-cyclohexadienimine], FD&C Blue No. 1 (disodium salt of dibenzyldiethyl-diamino-triphenylcarbinol trisulfonic acid anhydrite), FD&C Blue No. 2 (sodium salt of disulfonic acid of indigotin) and mixtures thereof in various proportions. Typically, colorants if included are present in very small quantities.

Flavoring agents are known, such as natural and artificial flavors. These flavorings may be chosen from synthetic flavor oils and flavoring aromatics, and/or oils, oleo resins and extracts derived from plants, leaves, flowers, fruits and so forth, and combinations thereof. Representative flavor oils include: spearmint oil, cinnamon oil, peppermint oil, clove oil, bay oil, thyme oil, cedar leaf oil, oil of nutmeg, oil of sage, and oil of bitter almonds. These flavoring agents can be used individually or in admixture. Commonly used flavors include mints such as peppermint, artificial vanilla, cinnamon derivatives, and various fruit flavors, whether employed individually or in admixture. Generally, any flavoring agent or food additive, such as those described in Chemicals Used in Food Processing, publication 1274 by the National Academy of Sciences, pages 63-258, may be used. Typically, flavoring agents, if included, are present at a concentration of from about 0.01 to about 1%, by weight. In some embodiments, the flavoring agent may be present at a concentration of about 0.2%, by weight.

Sweeteners include both natural and artificial sweeteners. Suitable sweeteners include water soluble sweetening agents such as monosaccharides, disaccharides and poysaccharides such as xylose, ribose, glucose (dextrose), mannose, galactose, fructose (levulose), sucrose (sugar), maltose, water soluble artificial sweeteners such as the soluble saccharin salts, i.e., sodium or calcium saccharin salts, cyclamate salts dipeptide based sweeteners, such a L-aspartic acid derived sweeteners, such as L-aspartyl-L-phenylalaine methyl ester (aspartame). In general, the effective amount of sweetener is utilized to provide the level of sweetness desired for a particular composition, will vary with the sweetener selected. This amount will normally be from about 0.001 to about 5%, by weight. In some embodiments, the sweetener is sodium saccharin and is present at a concentration of about 0.01%, by weight.

Whitening agents, material which is effective to effect whitening of a tooth surface to which it is applied, such as hydrogen peroxide and urea peroxide, high cleaning silica, preservatives, silicones, and chlorophyll compounds may be incorporated into the compositions of the present invention. In various embodiments, the compositions of this invention comprise a peroxide whitening agent, comprising a peroxide compound. A peroxide compound is an oxidizing compound comprising a bivalent oxygen-oxygen group. Peroxide compounds include peroxides and hydroperoxides, such as hydrogen peroxide, peroxides of alkali and alkaline earth metals, organic peroxy compounds, peroxy acids, pharmaceutically-acceptable salts thereof, and mixtures thereof. Peroxides of alkali and alkaline earth metals include lithium peroxide, potassium peroxide, sodium peroxide, magnesium peroxide, calcium peroxide, barium peroxide, and mixtures thereof. Organic peroxy compounds include carbamide peroxide (also known as urea hydrogen peroxide), glyceryl hydrogen peroxide, alkyl hydrogen peroxides, dialkyl peroxides, alkyl peroxy acids, peroxy esters, diacyl peroxides, benzoyl peroxide, and monoperoxyphthalate, and mixtures thereof. Peroxy acids and their salts include organic peroxy acids such as alkyl peroxy acids, and monoperoxyphthalate and mixtures thereof, as well as inorganic peroxy acid salts such as persulfate, dipersulfate, percarbonate, perphosphate, perborate and persilicate salts of alkali and alkaline earth metals such as lithium, potassium, sodium, magnesium, calcium and barium, and mixtures thereof. In various embodiments, the peroxide compound comprises hydrogen peroxide, urea peroxide, sodium percarbonate and mixtures thereof. In some embodiments, the peroxide compound comprises hydrogen peroxide. In some embodiments, the peroxide compound consists essentially of hydrogen peroxide. In some embodiments a non-peroxide whitening agent may be provided. Whitening agents among those useful herein include non-peroxy compounds, such as chlorine dioxide, chlorites and hypochlorites. Chlorites and hypochlorites include those of alkali and alkaline earth metals such as lithium, potassium, sodium, magnesium, calcium and barium. Non-peroxide whitening agents also include colorants, such as titanium dioxide and hydroxyapatite. One or more whitening agents are optionally present in a tooth-whitening effective total amount. In some embodiments the whitening agent is separated from the aqueous carrier. In some embodiments the whitening agent is separated from the aqueous carrier by encapsulation of the whitening agent.

Optionally, breath freshening agents may be provided. Any orally acceptable breath freshening agent can be used, including without limitation zinc salts such as zinc gluconate, zinc citrate and zinc chlorite, alpha-ionone and mixtures thereof. One or more breath freshening agents are optionally present in a breath freshening effective total amount.

Optionally, the composition may include a tartar control (anticalculus) agent. Tartar control agents among those useful herein include phosphates and polyphosphates (for example pyrophosphates), polyaminopropanesulfonic acid (AMPS), polyolefin sulfonates, polyolefin phosphates, diphosphonates such as azacycloalkane-2,2-diphosphonates (e.g., azacycloheptane-2,2-diphosphonic acid), N-methyl azacyclopentane-2,3-diphosphonic acid, ethane-1-hydroxy-1,1-diphosphonic acid (EHDP) and ethane-1-amino-1,1-diphosphonate, phosphonoalkane carboxylic acids and salts of any of these agents, for example their alkali metal and ammonium salts. Useful inorganic phosphate and polyphosphate salts include monobasic, dibasic and tribasic sodium phosphates, sodium tripolyphosphate, tetrapolyphosphate, mono-, di-, tri- and tetrasodium pyrophosphates, sodium trimetaphosphate, sodium hexametaphosphate and mixtures thereof, wherein sodium can optionally be replaced by potassium or ammonium. Other useful anticalculus agents include polycarboxylate polymers and polyvinyl methyl ether/maleic anhydride (PVME/MA) copolymers, such as those available under the Gantrez™ brand from ISP, Wayne, N.J. In some embodiments, a phosphate is present at a concentration of from about 0.01 to about 10%, by weight. In some embodiments, a phosphate is present at a concentration of from about 1%, by weight.

Some embodiments provide compositions wherein a buffering agent is present. In some embodiments, sodium phosphate monobasic is present at a concentration of from about 0.01 to about 5%, by weight. In some embodiments, sodium phosphate monobasic phosphate is present at a concentration of about 1%, by weight. In some embodiments, sodium phosphate dibasic is present at a concentration of from about 0.01 to about 5%, by weight. In some embodiments, sodium phosphate dibasic phosphate is present at a concentration of about 0.15%, by weight.

Other optional additives include antimicrobial (e.g., antibacterial) agents. Any orally acceptable antimicrobial agent can be used, including Triclosan (5-chloro-2-(2,4-dichlorophenoxy)phenol); 8-hydroxyquinoline and salts thereof, zinc and stannous ion sources such as zinc citrate, zinc sulphate, zinc glycinate, sodium zinc citrate and stannous pyrophosphate; copper (II) compounds such as copper (II) chloride, fluoride, sulfate and hydroxide; phthalic acid and salts thereof such as magnesium monopotassium phthalate; sanguinarine; quaternary ammonium compounds, such as alkylpyridinium chlorides (e.g., cetylpyridinium chloride (CPC), combinations of CPC with zinc and/or enzymes, tetradecylpyridinium chloride, and N-tetradecyl-4-ethylpyridinium chloride); bisguanides, such as chlorhexidine digluconate, hexetidine, octenidine, alexidine; halogenated bisphenolic compounds, such as 2,2' methylenebis-(4-chloro-6-bromophenol); benzalkonium chloride; salicylanilide, domiphen bromide; iodine; sulfonamides; bisguanides; phenolics; piperidino derivatives such as delmopinol and octapinol; magnolia extract; grapeseed extract; thymol; eugenol; menthol; geraniol; carvacrol; citral; eucalyptol; catechol; 4-allylcatechol; hexyl resorcinol; methyl salicylate; antibiotics such as augmentin, amoxicillin, tetracycline, doxycycline, minocycline, metronidazole, neomycin, kanamycin and clindamycin; and mixtures thereof. A further illustrative list of useful antibacterial agents is provided in U.S. Pat. No. 5,776,435, Gaffar, et al., issued Jul. 7, 1998. In some embodiments, the antimicrobial agent is present at a concentration of from about 0.001 to about 1%, by weight. In some embodiments, the antimicrobial agent is cetylpyridinium chloride. In some embodiments, cetylpyridinium chloride is present at a concentration of from about 0.001 to about 1%, by weight. In other embodiments, cetylpyridinium chloride is present at a concentration of about 0.05%, by weight.

Antioxidants are another class of optional additives. Any orally acceptable antioxidant can be used, including butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, and mixtures thereof.

Also optional, a saliva stimulating agent, useful for example in amelioration of dry mouth, may be included. Any orally acceptable saliva stimulating agent can be used, including without limitation food acids such as citric, lactic, malic, succinic, ascorbic, adipic, fumaric, and tartaric acids, and mixtures thereof. One or more saliva stimulating agents are optionally present in a saliva stimulating effective total amount.

Optionally, an antiplaque (e.g., plaque disrupting) agent may be included. Any orally acceptable antiplaque agent can be used, including without limitation stannous, copper, magnesium and strontium salts, dimethicone copolyols such as cetyl dimethicone copolyol, papain, glucoamylase, glucose oxidase, urea, calcium lactate, calcium glycerophosphate, strontium polyacrylates and mixtures thereof.

Optional desensitizing agents include potassium citrate, potassium chloride, potassium tartrate, potassium bicarbonate, potassium oxalate, potassium nitrate, strontium salts, and mixtures thereof.

Optional additives also include vitamins, herbs and proteins. Vitamins include Vitamins C and D, thiamine, riboflavin, calcium pantothenate, niacin, folic acid, nicotinamide, pyridoxine, cyanocobalamin, para-aminobenzoic acid, bioflavonoids, pantheon, retinyl palmitate, tocopherol acetate, and mixtures thereof. Herbs such as *Chamomilla recutita*, *Mentha piperita*, *Salvia officinalis*, and *Commiphora myrrha* may optionally be included. Suitable proteins include milk proteins and enzymes such as peroxide-producing enzymes, amylase, plaque-disrupting agents such as papain, glucoamylase, glucose oxidase, and "next generation" enzymes."

In some embodiments, trimethylglycine may be included in the composition. Trimethylglycine is a zwitterionic material that is a mucoadhesive humectant. It can enhance lubricity and provide a smooth pleasant mouthfeel. The inclusion of effective amounts of trimethylglycine is optional.

Suspended Solids and Particulates

In some embodiments, the fluid compositions allow for the suspension of particulates, insoluble materials and colloidals which would otherwise precipitate shortly after being suspended in an aqueous medium. The polymer mixture forms a structure which, while having a network formed by the polymer mixture sufficient to maintain solid particles in suspension, remains in a fluid state. Examples of suspended solid forms include insoluble flakes, specks, beads, and particulates. In some embodiments, solid particles comprising zinc oxide are incorporated directly into a structured fluid composition as described herein.

U.S. Pat. No. 6,669,929 generally describes examples of polymer matrix films and how they are produced. Polymer matrix films can be used as carriers for numerous types of active ingredients, particularly those that may be insoluble or reactive with components in the aqueous vehicle. Polymer matrix films comprising from about 30 to about 60%, by weight, zinc oxide are particularly useful to deliver zinc oxide in a fluid composition. In some embodiments, polymer matrix films comprise approximately 50%, by weight, zinc oxide.

Polymer matrix films may be included in the compositions described herein, at various concentrations. Typically, polymer matrix films are present at a concentration of about 0.25%, by weight, or more. Similarly, polymer matrix films are present in a concentration of about 3%, by weight, or less. In some embodiments, polymer matrix films are present at a concentration of from about 1% to about 2%, by weight.

Some embodiments of the present invention provide a water-stable film, comprising: one or more cellulosic polymers present in an amount from about 10 to about 50% of the film's dry weight; polyvinyl acetate present in an amount from about 8 to about 25% of the film's dry weight; and metal particles.

In some embodiments, the polyvinyl acetate is present at a concentration of from about 10 to about 20% of the film's dry weight. In some embodiments, the polyvinyl acetate is present at a concentration of about 10%, of the film's dry weight. In some embodiments, the polyvinyl acetate is present at a concentration of about 14%, of the film's dry weight. In some embodiments, the polyvinyl acetate is present at a concentration of about 18%, of the film's dry weight.

Some embodiments provide a film wherein the one or more cellulosic polymers are present at a concentration of from about 15 to about 30%, of the film's dry weight. Other embodiments provide a film wherein the one or more cellulosic polymers are present at a concentration of from about 18 to about 22%, of the film's dry weight.

Embodiments of the present invention are further described in the following examples. The examples are merely illustrative and do not in any way limit the scope of the invention as described and claimed.

EXAMPLES

Example 1

Exemplary compositions of the present invention are listed in Tables 1 and 2. The structuring agents utilized provide viscoelasticity and structure to the fluid compositions. When introduced to an aqueous system such as a mouthwash, the structuring agents form a network within the aqueous carrier, making the mouthwash a viscoelastic, shear thinning solution. The types of polymers, particles and combinations thereof can include any polymer or particle that is able to form by itself, or in combination with other polymers/particles, a structured network with the specific rheology profile.

The formulations of four exemplary compositions of the present invention are provided in Table 1 (below).

TABLE 1

| Ingredient | I % w/w | II % w/w | III % w/w | IV % w/w | Conc. Range % w/w |
|---|---|---|---|---|---|
| Water | 72.4 | 72.3 | 72.4 | 72.3 | 40-97 |
| Humectants | 17.5 | 17.5 | 17.5 | 17.5 | 1-25 |
| Surfactant | 1 | 1 | 1 | 1 | 0.01-10 |
| Sodium phosphate monobasic | 1 | 1 | 1 | 1 | 0.01-5 |
| Disodium phosphate | 0.15 | 0.15 | 0.15 | 0.15 | 0.01-5 |
| Preservative | 0.5 | 0.5 | 0.5 | 0.5 | 0.01-1 |
| Flavor | 0.2 | 0.2 | 0.2 | 0.2 | 0.01-1 |
| Gum-type colloidal | 0.083 | 0.083 | 0.041 | 0.083 | 0.01-5 |
| Cellulosic Polymer | 0.083 | 0.083 | 0.03 | 0.083 | 0.01-5 |
| Acrylate Polymer | 0.05 | 0.05 | 0.05 | 0.05 | 0.01-5 |
| Gum-type colloidal | — | 0.05 | — | — | 0.01-5 |
| Clay | — | — | — | 0.05 | 0.01-2 |
| Sodium fluoride | 0.02 | 0.02 | 0.02 | 0.02 | — |
| Sweetener | 0.01 | 0.01 | 0.01 | 0.01 | 0.001-0.5 |
| Cetylpyridinium chloride | 0.05 | 0.05 | 0.05 | 0.05 | 0.001-1 |

The rheology parameters described herein have been quantified for three exemplary compositions of the present invention (Compositions I-III), as well as for several commercial products.

Composition I contains one gum type colloidal polymer, one cellulosic polymer, and one acrylate polymer. Composition I contains, in part, 0.083%, by weight, xanthan gum; 0.083%, by weight, carboxymethyl cellulose; and 0.05%, by weight, acrylate polymer.

Composition II contains the same structuring agents in the same concentrations as Composition I, but also includes an additional structuring agent—a second gum type colloidal polymer, gellan gum at a concentration of 0.05%, by weight.

Composition III contains one gum type colloidal polymer, one cellulosic polymer, and one acrylate polymer. Composition III contains, in part, 0.041%, by weight, xanthan gum; 0.03%, by weight, carboxymethyl cellulose; and 0.05%, by weight, acrylate.

All three compositions yield rheology parameters that are within the specified ranges that define a structured non-solid composition (G'/G"≥1). A structured composition provides a significant advantage in suspending non-density matched solids in a fluid composition. All three compositions also yield rheology parameters that constitute a viscoelastic, shear thinning non-solid composition (Flow Rate Index from about 0.1 to about 0.8), with a Consistency Index of from about 10 to about 2000. A viscoelastic, shear thinning fluid composition has a significant advantage in terms of providing a differentiating mouth feel as well as the ability to deposit a polymer film onto oral cavity surfaces to facilitate the delivery of actives.

Table 2 (below) describes rheology parameters used to characterize the unique properties of three exemplary compositions of the present invention (Compositions I-III), in comparison to the rheology parameters of several commercially available products (Comparative Examples 1-7).

TABLE 2

| | Strain Sweep | | | | |
|---|---|---|---|---|---|
| | G' | G" | Structural Parameter | Power Law Fit | |
| Composition | (dyn/cm2) | (dyn/cm2) | (G'/G") | n | k (cps) |
| I | 8.25 | 5.57 | 1.48 | 0.5 | 163.5 |
| II | 365.6 | 46.93 | 7.96 | 0.4 | 382.7 |
| III | 85.09 | 16.24 | 5.24 | 0.7 | 62.7 |
| Comp Ex 1 | 0.01 | 2.25 | 0.01 | 1 | 25.7 |
| Comp Ex 2 | 0.01 | 0.41 | 0.02 | 1 | 8.8 |
| Comp Ex 3 | 0.11 | 0.38 | 0.29 | 1 | 2.2 |
| Comp Ex 4 | 0.16 | 0.37 | 0.43 | 1 | 2.6 |
| Comp Ex 5 | 0.06 | 0.34 | 0.17 | 1 | 2.7 |
| Comp Ex 6 | 0.01 | 0.35 | 0.03 | 1 | 2.6 |
| Comp Ex 7 | 0.42 | 0.83 | 0.51 | 1 | 2.2 |

Comparative Example 1 (Comp Ex 1) contains the following ingredients: water, xylitol, hydrogenated starch hydrolysate, propylene glycol, hydroxycellulose, aloe vera (*Aloe Barbadensis*) Leaf Juice, flavor, Poloxamer 407, calcium lactate, zinc gluconate, sodium benzoate, benzoic acid, potassium thiocyanate, and enzymes (Lactoferrin, Lysozyme, Lactoperoxidase, Glucose Oxydase).

Comparative Example 2 (Comp Ex 2) contains the following ingredients: water, glycerin, sorbitol, poloxamer 338, PEG-60 hydrogenated castor oil, carboxymethylcellulose, cetylpyridinium chloride, copovidone, propylparaben, sodium benzoate, sodium phosphate, sodium saccharin, xanthan gum, and FD&C blue no. 1.

Comparative Example 3 (Comp Ex 3) contains the following ingredients: water, glycerin, alcohol, propylene glycol, sorbitol, polysorbate 20, flavor, sodium benzoate, cetylpyridinium chloride, sodium saccharin, D&C yellow no. 10, and FD&C blue no. 1.

Comparative Example 4 (Comp Ex 4) contains the following ingredients: water, glycerin, sorbitol, propylene glycol, poloxamer 407, monosodium phosphate, sodium benzoate, disodium phosphate, flavor, cetylpyridinium chloride, sodium fluoride, sodium saccharin, FD&C green no. 3, and FD&C yellow no. 5.

Comparative Example 5 (Comp Ex 5) contains the following ingredients: water, sorbiotol solution, monosodium phosphate, poloxamer 338, flavor, potassium sorbate, phosphoric acid, sodium fluoride, polysorbate 20, FD&C blue no. 1.

Comparative Example 6 (Comp Ex 6) contains the following ingredients: water, alcohol, benzoic acid, poloxamer 407, sodium benzoate, caramel color, eucalyptol, menthol, methyl salicylate, and thymol.

Comparative Example 7 (Comp Ex 7) contains the following ingredients: calcium disodium EDTA, cetylpyridinium chloride, disodium phosphate, flavor, green 3, menthol, methyl salicylate, poloxamer 407, polysorbate 20, potassium sorbate, propylene glycol, sodium benzoate, sodium phosphate, sodium saccharin, sorbitol, water, yellow 5, and sodium fluoride.

Example 2

Rheology Analyses

Rheology is of paramount importance in characterizing viscoelastic formulations since rheological parameters often provide great insight into the structural and mechanical properties that are crucial to obtaining the desired product performance. Rheology data is often used to quantify consumer preference for one product over another, to ensure good manufacturing and stability properties, to gauge suspending capabilities, just to name a few applications. Nowadays, rheology experiments can be conducted in a variety of commercial rheometers, for example stress or strain controlled instruments, with a variety of geometries ranging from a cone-and-plate, to parallel plate, to cuettes or concentric cylinders. In the determination of which rheometer and geometry to use, one must take into consideration the type of system at hand (e.g., gel or paste, low- or high-viscosity fluid) as well as the type of information that needs to be acquired.

Experiments conducted as part of this work may be performed in a stress controlled AR2000 rheometer (TA Instruments), using a cone and plate geometry. A peltier is used to control the temperature and a solvent trap is used to prevent sample evaporation. All experiments are performed at 25±0.1° C.

Strain Sweep Experiment

The linear viscoelastic behavior of structured fluid compositions such as the ones described herein can be quantified through dynamic oscillatory experiments such as frequency and strain sweeps.

In a strain sweep experiment, the amplitude of the applied strain varies in the range 0.1%<γ<100% while the frequency of oscillations is kept constant. The viscoelastic response of the material to the applied oscillatory strain is measured in terms of G' and G", the viscous and loss moduli and other valuable information is obtained this way. In general, G' represents energy storage within the viscoelastic structure and G" represents dissipation of this energy through flow. The linear viscoelastic region (LVR) is determined by the region of the strain sweep in which G' and G" remain constant with respect to the applied strain and the ratio of elastic to viscous contribution (G'/G") can be calculated based on the G' and G" values within the LVR. This ratio provides a good indication of how structured a fluid composition is, with a higher G'/G" ratio indicating that a more robust structure is present within the system. The yield stress value is also determined from a strain sweep experiment, by plotting the elastic stress (G'×Strain) vs. Strain. The yield stress is then the maximum in the elastic stress.

With this information in hand one can determine whether a certain viscoelastic material exhibits more solid-like or more fluid-like properties, and in this particular case the data can be utilized effectively to determine whether various aesthetics and solid materials can be successfully suspended within the fluid composition.

Steady State Flow Experiment

Just as structural properties are characterized by oscillatory experiments, flow properties of different materials can be characterized through steady state shearing. In a steady state flow experiment a range of strains (shear rates) is applied to the sample and the viscosity, and/or resulting shear stress are plotted as a function of the applied shear rate. Flow curves may be obtained in the shear rate range of 0.1-100 sec$^{-1}$, for example. The viscosity at a single, arbitrary shear rate can then be used to characterize a particular sample and compare it to other samples.

Example 3

Table 3 (below) provides the formulation of another exemplary composition of the present invention (Composition V).

TABLE 3

| Ingredient | % w/w |
|---|---|
| Water | 71.96 |
| Vegetable Glycerin | 7.5 |
| Ethyl Alcohol | 6 |
| Sorbitol (70% Solution) | 5.5 |
| Propylene Glycol | 5 |
| Polysorbate 20 | 2 |
| Anhydrous Disodium Phosphate | 0.75 |
| Flavor | 0.4 |
| Sodium Benzoate | 0.25 |
| Cetylpyridinium Chloride | 0.05 |
| Gellan Gum | 0.05 |
| Sodium Fluoride | 0.05 |
| Sodium Saccharin | 0.05 |
| Xanthan Gum | — |
| Simethicone Emulsion | 0.001 |

Table 4 (below) describes rheology parameters used to characterize the unique properties of Composition V.

TABLE 4

| | Strain Sweep | | | Power Law Fit | |
|---|---|---|---|---|---|
| Composition | G' (dyn/cm2) | G" (dyn/cm2) | Structural Parameter (G'/G") | n | k (cps) |
| V | 63.6 | 11.3 | 5.7 | 0.45 | 359 |

Example 4

Process

A composition of the present invention may be made using a process in which the gellan and xanthan gums are first hydrated and mixed with salt at an elevated temperature and then mixed with the remaining ingredients after cooling. Water is initially heated to a temperature sufficient to hydrate said xanthan gum and said gellan gum. In some embodiments, the water is between 160° F. and 180° F. In some embodiments, the water is about 180° F.

The xanthan gum and gellan gum are then added to the heated water and maintained for a time and at a temperature sufficient to hydrate the xanthan gum and the gellan gum. In some embodiments, the mixture is between 160° F. and 180° F. In some embodiments, the water is about 180° F. In some embodiments, the mixture is maintained for at least about 3 minutes and no longer than 30 minutes. In some embodiments, the mixture is maintained for 5 to 15 minutes. In some embodiments, the mixture is maintained for about 15 minutes. The mixture may be mixed for all or part of the time it is maintained at the temperature sufficient to hydrate the xanthan gum and the gellan gum. In some embodiments, the mixture is mixed for at least about 3 minutes and no longer than 30 minutes. In some embodiments, the mixture is mixed for 5 to 15 minutes. In some embodiments, the mixture is mixed for about 15 minutes. Following this step, the mixture comprises hydrated gellan and xanthan gums. Sodium salt is then added to the mixture.

The mixture of hydrated gums and sodium salt is allowed to cool to a temperature of about 125° F. or less. In some embodiments, the mixture of hydrated gums and sodium salt is cooled to a temperature between 75 to 110° F. In some embodiments, the mixture of hydrated gums and sodium salt is cooled to about 75° F., room temperature. In some embodiments, the mixture of hydrated gums and sodium salt is mixed for all or part of the time it is cooling. In some embodiments, mixing is discontinued during the entire cooling.

Once the mixture has cooled, the remaining ingredients are added to the cooled mixture to produce a combined composition. In some embodiments, the remaining ingredients include solid particles such as polymer matrix films. The combined composition is mixed to incorporate the added ingredients, preferably essentially to a homogenous degree. In some embodiments, the combined composition is mixed for 10 to 30 minutes to produce said fluid composition. In some embodiments, the combined composition is mixed for about 15 minutes to produce said fluid composition. The combined composition may be preferably mixed at a low or medium speed to avoid foaming. In some embodiments, the combined composition is mixed at a medium speed to avoid foaming.

As those skilled in the art will appreciate, numerous changes and modifications may be made to the embodiments described herein without departing from the spirit of the invention. It is intended that all such variations fall within the scope of the appended claims.

What is claimed is:

1. A fluid composition comprising:
structuring agents consisting of:
a colloidal gum;
a cellulosic polymer;
an acrylate polymer; and
a clay or fine particulate; and
an orally acceptable aqueous carrier;
wherein the total concentration of the structuring agents is from about 0.03% to about 2%, by weight, of the composition;
wherein the composition is a mouthwash or mouthrinse,
wherein the composition has a Flow Rate Index from about 0.1 to about 0.85, a Consistency Index of from about 10 to about 2000 and a G'/G" ratio of 1 to 15;
wherein the colloidal gum comprises is xanthan gum in an amount of from about 0.01 to about 0.5%, by weight; and
wherein the clay or fine particulate is selected from calcium magnesium silicate or amorphous silica, and is present in a concentration of 0.5%, by weight;
wherein the cellulosic polymer comprises is carboxymethyl cellulose in an amount of from about 0.01 to about 0.5%, by weight; and
wherein the acrylate polymer is present in an amount of from about 0.01 to about 0.5%, by weight.

2. The composition of claim 1, further comprising a humectant selected from: sorbitol, glycerin, propylene glycol, ethanol, or a combination of two or more thereof.

3. The composition of claim 1, wherein the orally acceptable aqueous carrier comprises greater than 50%, by weight, free water.

4. The composition of claim 1, further comprising one or more components selected from a fluoride ion source; a tartar control agent; a buffering agent; an abrasive; or a combination of two or more thereof.

5. The composition of claim 4, wherein the fluoride ion source is selected from: stannous fluoride, sodium fluoride, potassium fluoride, sodium monofluorophosphate, sodium fluorosilicate, ammonium fluorosilicate, amine fluoride, ammonium fluoride, or a combination of two or more thereof.

6. The composition of claim 1, wherein the structuring agents consist of:
from about 0.03 to about 0.1%, by weight, of xanthan gum;
from about 0.02 to about 0.1%, by weight, of carboxymethyl cellulose;
from about 0.03 to about 0.1%, by weight, of an acrylate polymer; and 0.5%, by weight of clay or fine particulate.

7. The composition of claim 1, further comprising a suspended material.

8. The composition of claim 7, wherein said suspended material is selected from: a colloidal metal; a film flake; a film strip; or a combination of two or more thereof.

9. The composition of claim 2, wherein the orally acceptable aqueous carrier comprises greater than 50%, by weight, free water.

10. The composition of claim 9, wherein the structuring agents consist of:
from about 0.03 to about 0.1%, by weight, of xanthan gum;
from about 0.02 to about 0.1%, by weight, of carboxymethyl cellulose; and
from about 0.03 to about 0.1%, by weight, of an acrylate polymer; and 0.5%, by weight of clay or fine particulate.

11. The composition of claim 10, further comprising one or more components selected from a fluoride ion source; a tartar control agent; a buffering agent; an abrasive; or a combination of two or more thereof.

12. The composition of claim 11, wherein the fluoride ion source is selected from: stannous fluoride, sodium fluoride, potassium fluoride, sodium monofluorophosphate, sodium fluorosilicate, ammonium fluorosilicate, amine fluoride, ammonium fluoride, or a combination of two or more thereof.

* * * * *

UNITED STATES PATENT AND TRADEMARK OFFICE
CERTIFICATE OF CORRECTION

PATENT NO. : 11,147,751 B2
APPLICATION NO. : 13/997344
DATED : October 19, 2021
INVENTOR(S) : Paloma Pimenta et al.

It is certified that error appears in the above-identified patent and that said Letters Patent is hereby corrected as shown below:

In the Specification

In Column 3, Line 7, delete "04%," and insert -- 0.4%, --, therefor.

In the Claims

In Column 17, Line 38, in Claim 1, delete "comprises".

In Column 17, Lines 39-42, in Claim 1, delete "and wherein the clay or fine particulate is selected from calcium magnesium silicate or amorphous silica, and is present in a concentration of 0.5%, by weight;".

In Column 17, Line 43, in Claim 1, delete "comprises".

In Column 17, Line 47, in Claim 1, after "by weight", delete "." and insert -- ; and wherein the clay or fine particulate is selected from calcium magnesium silicate or amorphous silica, and is present in a concentration of 0.5%, by weight. --, therefor.

In Column 18, Line 36, in Claim 10, delete "and".

Signed and Sealed this
Eleventh Day of January, 2022

Drew Hirshfeld
*Performing the Functions and Duties of the*
*Under Secretary of Commerce for Intellectual Property and*
*Director of the United States Patent and Trademark Office*